(12) United States Patent
Higuchi et al.

(10) Patent No.: US 6,413,211 B2
(45) Date of Patent: Jul. 2, 2002

(54) ELECTRONIC-ENDOSCOPE LIGHT SOURCE UNIT FOR SETTING SHADING PERIOD

(75) Inventors: Mitsuru Higuchi; Daisuke Ayame; Kazuhiro Yamanaka; Shinji Takeuchi, all of Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/897,971

(22) Filed: Jul. 5, 2001

Related U.S. Application Data

(62) Division of application No. 09/274,301, filed on Mar. 23, 1999.

(30) Foreign Application Priority Data

Mar. 25, 1998 (JP) .............................................. 10-96785
Mar. 30, 1998 (JP) ........................................... 10-103792
Mar. 30, 1998 (JP) ........................................... 10-103793

(51) Int. Cl.$^7$ ................................................ A61B 1/06
(52) U.S. Cl. ......................... 600/181; 600/186; 348/68; 362/574
(58) Field of Search ................................ 600/180, 181, 600/109, 160; 348/68, 69, 22, 220, 221; 362/574

(56) References Cited

U.S. PATENT DOCUMENTS 4,704,520 A * 11/1987 Kanno et al. ................ 250/205
4,729,018 A * 3/1988 Watanabe et al. ........... 348/368
4,791,480 A * 12/1988 Muranaka .................... 348/230

* cited by examiner

*Primary Examiner*—John Mulcahy
(74) *Attorney, Agent, or Firm*—Snider & Associates; Ronald R. Snider

(57) ABSTRACT

The present invention is a unit for eliminating the fluctuation of luminous energy reduction by keeping the response time of a shading mechanism constant even if a diaphragm opening degree differs when reading every pixel by setting a shading period. This unit is provided with a shading mask having a quadrangular or V-shaped opening and moves a shading shutter in the horizontal direction perpendicular to the vertically moving direction of a diaphragm plate. Therefore, a shading period is set in accordance with the constant response time of the shading shutter and the rate of luminous energy reduction becomes constant. Moreover, a high-quality static image having a stable brightness can be obtained by reading the signal of every pixel obtained by a CCD through one-time exposure while using the shading period and then pixel-mixing signals. Furthermore, it is possible to use the Archimedean spiral for the outer periphery of the diaphragm plate or the shading shutter.

3 Claims, 11 Drawing Sheets

FIG.3(A) O/E SIGNAL
FIG.3(B) SHADING-PLATE SHUTTER
FIG.3(C) OPTICAL OUTPUT
FIG.3(D) READ PULSE P1 (ODD LINE)
FIG.3(E) READ PULSE P2 (EVEN LINE)
FIG.3(F) ELECTRONIC SHUTTER

FIG. 4
FIG.4(A)
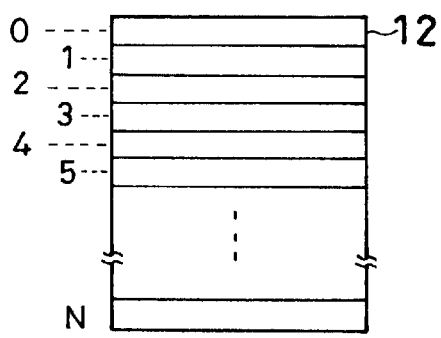
FIG.4(B)         FIG.4(C)
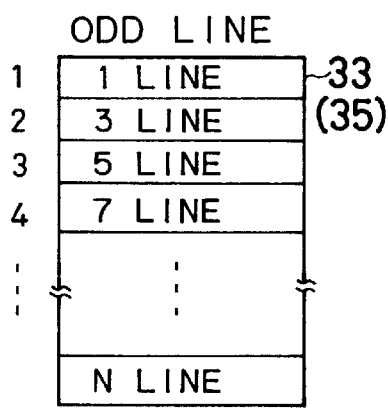    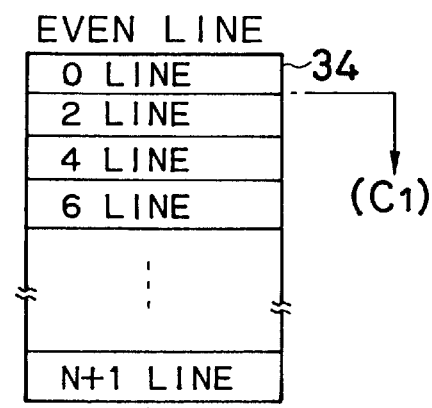
FIG.4(D)         FIG.4(E)
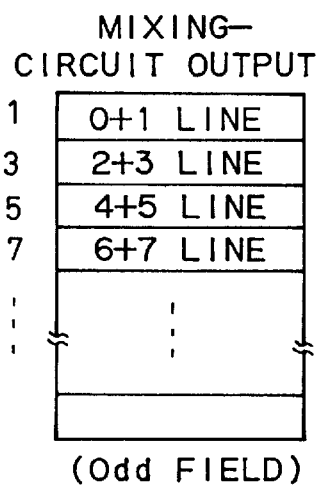    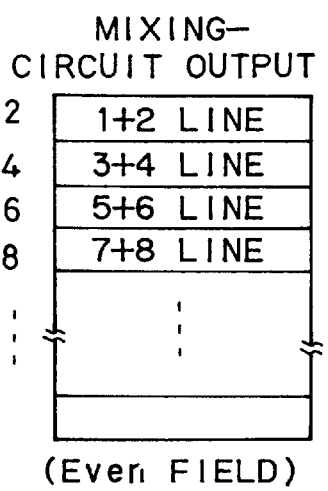

ELECTRONIC-ENDOSCOPE LIGHT SOURCE UNIT FOR SETTING SHADING PERIOD

This application is a Divisional of application Ser. No. 09/274,301, filed on Mar. 23, 1999.

BACKGROUND OF THE INVENTION

This application claims the priority of Japanese Patent Application No. 10-96785 filed on Mar. 25, 1998 and Nos. 10-103792 and 10-103793 filed on Mar. 30, 1998 which are incorporated herein by reference.

1. Field of the Invention

The present invention relates to an electronic-endoscope light source unit, particularly to a structure for adjusting the luminous energy of video signals for reading every pixel by an electronic endoscope for reading the signal of every pixel accumulated in an image pickup device by setting a shading period.

2. Description of the Prior Art

In the case of an electronic endoscope system, a video signal is formed by reading electric charges accumulated by a photoelectric conversion device in pixels by a CCD (Charge Coupled Device) serving as a solid-state image pickup device. Moreover, in the case of a simultaneous-type electronic endoscope system, color filters are arranged on the CCD in pixels and thereby, a color image can be obtained.

FIG. 14 shows how the color filters are arranged. As shown in FIG. 14, Mg (magenta) and Cy (cyanogen) pixels are arranged on even lines of the image pickup face of a CCD 1 in pixels and G (green) and Ye (yellow) pixels are arranged on odd lines of it in pixels. The CCD 1 makes it possible to obtain accumulated electric charges (pixel signals) in pixels through these color filters.

Moreover, according to a conventional mixing read mode, accumulated electric charges of the pixels on upper and lower lines of the CCD 1 are added and mixed with each other and read. For example, in the case of the electric charges accumulated through the first-time exposure in a period of 1/60 sec (vertical sync period), video signals in odd fields such as a mixed signal of lines 0 and 1, a mixed signal of lines 2 and 3, . . . are read as shown at the left side of FIG. 14. In the case of the electric charges accumulated through the second-time exposure in a period of 1/60 sec, video signals in even fields such as a mixed signal of lines 1 and 2, a mixed signal of lines 3 and 4, . . . are read as shown at the right side of FIG. 14.

Therefore, a two-line mixed signal of the CCD 1 becomes a one-line signal of a field image and an odd-field signal and an even-field signal read by shifting one line are alternately output every exposure in a period of 1/60 sec. These odd-field and even-field signals are interlaced and scanned to form a one-frame image and the one-frame image is displayed on a monitor as a dynamic or static image.

BRIEF SUMMARY OF THE INVENTION

Object of the Invention

However, the above simultaneous electronic endoscope system has a problem that the quality (resolution or color shift) of, particularly, a static image is deteriorated if there is a time shift of 1/60 sec between an odd-field signal and an even-field signal for forming a one-frame image and an endoscope or an object to be observed is moved during the time shift.

Therefore, the present applicant uses an every-pixel read mode for reading the data for every pixel obtained through one-time exposure immediately before by setting and using a predetermined shading period. However, by driving a shading shutter for setting the shading period, a mechanical (such as a gear) response delay occurs. That is, because a complete shading state is necessary for the shading period for reading data, the shading shutter is operated slightly before the shading period by considering the response time. In this case, the luminous energy for the exposure immediately before is reduced due to the then response operation (operation until complete shading is realized). Moreover, when adjusting the luminous energy emitted from a light source by a diaphragming mechanism, problems occur that the response time of the shading shutter changes depending on the opening state of the diaphragm and insufficient luminous energy changes.

FIG. 15 shows the relation between diaphragm member of a diaphragming mechanism and shading shutter for setting a shading period. For example, a diaphragm vane 3 and a shading shutter 4 are arranged so as to be able to shade a luminous flux (diaphragm opening) 100 from a light source. In this case, the diaphragm vane 3 is set so as to rotate about a rotary axis 3A and the shading shutter 4 is set so as to rotate about a rotary axis 4A clockwise. Moreover, the diaphragm vane 3 is driven so that the brightness signal of a video signal becomes constant. For example, by increasing luminous energy at a far point and reducing it at a near point, a preferable image can be obtained. Moreover, by rotating the shading shutter 4 one turn at a predetermined rotational speed, the shutter 4 is moved so as to completely shade the luminous flux 100 for a period of 1/60 sec.

In the case of the above structure, however, because the diaphragm vane 3 and shading shutter 4 are rotated in the same direction, the timing for the shading shutter 4 to shade an actual luminous flux 100P depends on the driving position of the diaphragm vane 3 and the response time for completely shading the luminous flux 100P changes. That is, in FIG. 15, to completely shade the actual luminous flux loop, the shading shutter 4 rotates by a rotational angle of θ1 when the diaphragm vane 3 fully opens, by a rotational angle of θ2 when the diaphragm vane 3 is present at the continuous line, and by a rotational angle of θ3 when the diaphragm vane 3 is present at the two-dot chain line and resultantly, the response time is changed.

FIG. 16 shows the relation between luminous energy C (light quantity) of the luminous flux 100 and response time (luminous energy is assigned to vertical axis and time is assigned to horizontal axis). This diagram compares a case in which the diaphragm vane 3 fully opens and the response time ta1 when completely shading the luminous flux 100 is equal to 2 mS (sec) with a case in which the diaphragm vane 3 is present at a position for shading the half of a diaphragm opening 2 and the response time ta2 when shading the remaining half of the luminous flux 100 is equal to 1 mS.

In this case, when the diaphragm fully opens and the response time ta1 is equal to 2 mS, the electric charge quantity to be accumulated by the CCD 1 is normally shown by the following expression by assuming the luminous energy C for unit time when the diaphragm fully opens as 4 V and the exposure time (tb) as 1/60 sec.

$$tb \times C = 1/60 [mS] \times 4[V] \approx 66.67 [mVs]$$

Moreover, the electric charge quantity when setting a shading period is obtained as shown below by assuming an attenuation line at the response time ta1 as a straight line.

$$tb \times C - (1/2) ta1 \times C = 1/60 [mS] \times 4[V] - (1/2) \cdot 2[mS] \times 4[V] \approx 62.67 [mVS]$$

Therefore, the luminous energy when setting a shading period is reduced to 94% of the normal luminous energy (luminous energy reduction of 6%) and also, the brightness of an image lowers by 6%.

However, when the diaphragm half opens and the response time ta2 is equal to 1 mS, the electric charge quantity accumulated by the CCD 1 is normally obtained as shown below by assuming the luminous energy C in this case as 2 V and the exposure time (tb) as $\frac{1}{60}$ sec.

$$tb \times C = \frac{1}{60}[mS] \times 2[V] = 33.33[mVS]$$

Thus, the electric charge quantity when setting a shading period is obtained as shown below.

$$tb \times C - (\frac{1}{2})ta2 \times C = \frac{1}{60}[mS] \times 2[V] - (\frac{1}{2}) \cdot 1[mS] \times 2[V] = 32.33[mVS]$$

Therefore, the luminous energy when setting a shading period is reduced to 97% of the normal luminous energy (luminous energy reduction of 3%) and the brightness of an image also lowers by 3%.

Thus, when the response times ta1 and ta2 are different from each other, the rates of reduction of photographing luminous energy are different from each other, the luminous energy reduction increases as the response time ta increases, and resultantly the image brightness changes.

SUMMARY OF THE INVENTION

The present invention is made to solve the above problems and its object is to provide an electronic-endoscope light source unit for setting a shading period, capable of eliminating the fluctuation of luminous energy reduction so that the response time of a shading mechanism becomes constant by an electronic endoscope for reading every pixel by setting the shading period even when a diaphragm opening degree differs.

To achieve the above object, an electronic-endoscope light source unit of the present invention includes first shading means for shading a light-source luminous flux in a predetermined shading direction and second shading means for shading the light-source luminous flux in a shading direction almost perpendicular to the shading direction of the first shading means to set a shading period by using one of the first shading means and the second shading means as a diaphragming mechanism and the other shading means as a fully-closed shading mechanism for setting a fully-closed shading period for reading the signal of every pixel accumulated in an image pickup device.

In the case of the above structure, it is possible to arrange a shading mask having a quadrate opening, move the diaphragm member of the diaphragming mechanism along two sides of top and bottom or right and left of the quadrate opening, and move the shading shutter of the full-closed shading mechanism along other two sides.

It is possible to apply the above light source unit to an electronic endoscope system for reading the signal of every pixel accumulated in a solid-state image pickup device by using a shading period. In this case, an image-pickup-device driving circuit is able to execute an under-image-pickup-device-outputting pixel-mixing read mode for mixing video signals accumulated in an image pickup device between upper and lower lines and outputting them to form a dynamic image and an every-pixel read mode for reading the signal of every pixel accumulated in the image pickup device through one-time exposure by using the shading period to form a static image.

According to the above structure, a shading mask having a rectangular opening is set, a diaphragm member moves along the right and left sides of the shading-mask rectangular opening, and a shading shutter moves along the top and bottom sides perpendicular to the right and left sides. Therefore, even if a diaphragm member is set to any diaphragm position, the time for the shading shutter to shade a light-source luminous flux, that is, the response time of the shading shutter becomes almost constant. As a result, a luminous-energy deficiency caused by the response time (response delay) becomes constant and the fluctuation of luminous energy reduction under the exposure immediately before setting a shading period is eliminated.

Then, a high-quality static image is formed through, for example, the every-pixel read mode. In the every-pixel read processing, for electric charges accumulated through the exposure in a predetermined (assumed as first) period (vertical sync period) of $\frac{1}{60}$ sec, odd lines of an image pickup device are read in the second period ($\frac{1}{60}$ sec), remaining even lines are read in the third (next exposure) period, and these data values are stored in a predetermined memory. Moreover, the second period is set as a shading period so that the even lines can be read.

That is, when electric charges for the next exposure are accumulated in the second period for reading accumulated electric charges of the odd lines as ever, it is impossible to read remaining even lines. Therefore, accumulated electric charges of even lines are read in the third period by using the second period as a shading period. Thereby, it is possible to read the signal of every pixel of an image pickup device obtained through one-time exposure.

Then, video signals of odd lines and even lines stored in the memory are adjusted in phase and then, pixel mixing is performed between odd and even lines by a mixing circuit. That is, the pixel mixing forms a signal equivalent to the case of the under-image-pickup-device-outputting pixel-mixing read mode executed when a signal is output from an image pickup device. However, the signal is different from the case of the under-image-pickup-device-outputting pixel-mixing read mode in that pixel mixing is performed in accordance with the data obtained through one-time exposure.

When a dynamic image is normally displayed, the under-image-pickup-device-outputting pixel-mixing read mode is selected and pixels of two horizontal lines are mixed and read when output from an image pickup device as ever. Therefore, it is possible to obtain a dynamic image accurately reproducing the movement of an object through the image pickup with time.

Moreover, another invention has a shading member whose outer periphery is formed into the Archimedean spiral as the above second shading means to move the outer periphery of the shading member in the direction perpendicular to the shading direction of the above first shading means.

According to the above structure, by rotating the shading member of the second shading means, the shading member shades a circular luminous flux while the outer periphery of the Archimedean spiral almost linearly moves in a predetermined direction of the luminous flux. Moreover, when using the second shading means as a full-closed shading mechanism and the first shading means as a diaphragming mechanism, a shading shutter is set so that the outer periphery of the Archimedean spiral moves in a direction almost perpendicular to the rotational direction of a diaphragm vane. Thereby, even if the diaphragm vane moves to any diaphragm position, the shading shutter completely shades light-source luminous fluxes at almost the same time and the response time of the shading shutter becomes constant. As a result, the luminous energy deficiency caused by the response (response delay) time becomes constant and the fluctuation of the luminous-energy reduction at the time of the exposure immediately before setting a shading period is eliminated.

Still another invention is provided with a shading mask for controlling the passing range of a light-source luminous flux with an almost-V-shaped opening, a shading member for rotating about the V-shape intersection of the opening of the shading mask, first shading means for shading the V-shaped opening in accordance with the rotation of the shading member, and a shading member for moving in a direction almost perpendicular to the rotational direction of the first shading means, includes second shading means for shading the V-shaped opening by the shading member, and uses one of the first shading means and second shading means as a diaphragming mechanism and the other shading means to set a full-closed shading period for reading the signal of every pixel accumulated in an image pickup device. For example, it is possible to use the first shading means as a full-closed shading mechanism and the second shading means as a diaphragming mechanism. Moreover, it is possible to use means having a shading member whose outer periphery is formed like the Archimedean spiral as the first or second shading means.

Also, the present light source unit makes it possible to form a dynamic image in accordance with the under-image-pickup-device-outputting pixel-mixing read mode and form a static image in accordance with the every-pixel read mode.

According to the above structure, the rotation axis of the fan-shaped shading shutter of the full-closed shading mechanism is set to the V-shape intersection of the opening of the shading mask and the shading shutter rotates from one side toward the other side of the V shape of the opening. However, the diaphragm plate of the diaphragming mechanism linearly moves from the V-shaped-opening expanded side (upper side) toward the intersection. Thereby, even if the diaphragm plate moves to any diaphragm position, the shading shutter rotates by the V-shape opening angle whenever completely shading a light-source luminous flux and thereby, the luminous-flux shading time, that is, the response time of the shading shutter becomes constant. As a result, the luminous energy deficiency caused by the response (response delay) time becomes constant and the fluctuation of the luminous energy reduction under the exposure immediately before setting a shading period is eliminated.

BRIEF DESCRIPTION OF THE DRAWINGS

FIGS. 4(A) to 4(E) are illustrations showing the video data read between the CCD and the mixing circuit in FIG. 1;

DATAILED DESCRIPTION OF THE PREFERRED EMBODIMENTS

First Embodiment

Figure 1:
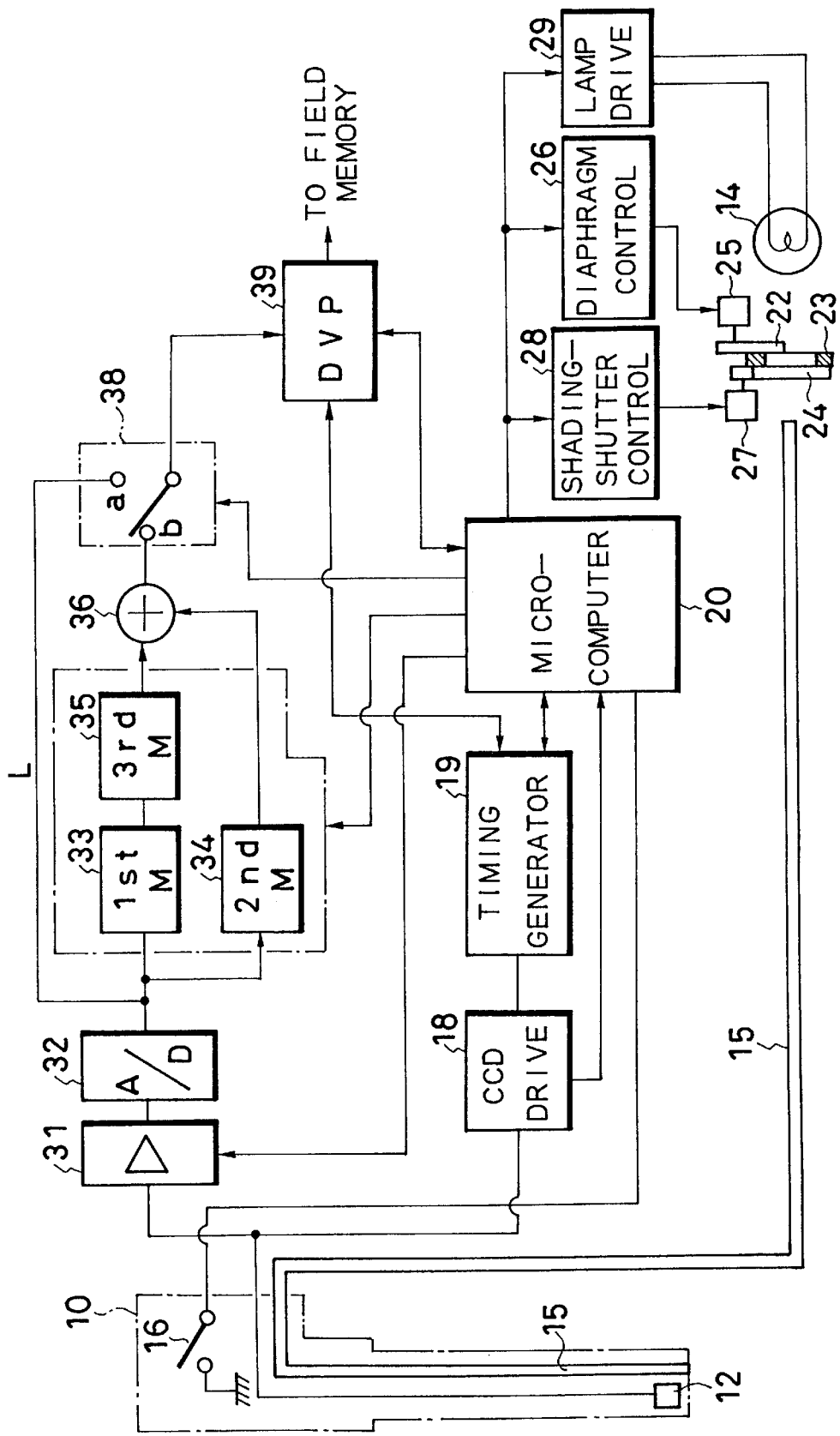
FIG. 1 is a block diagram showing the entire structure of an electronic endoscope system to which the light source unit of the first embodiment of the present invention is applied.
Figure 14:
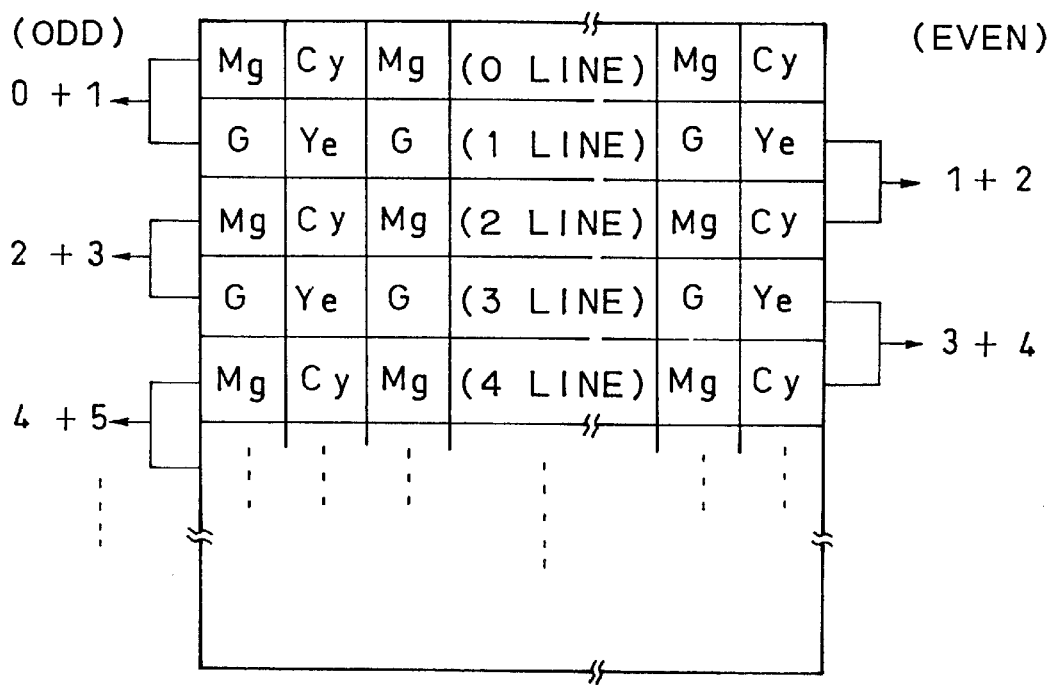
FIG. 14 is an illustration for explaining the arrangement of color filters and the pixel mixing read of a conventional CCD.

FIG. 1 shows the structure of an electronic endoscope system to which a light source unit of the present embodiment is applied. The electronic endoscope system is constituted by connecting a scope (electronic endoscope) 10 to a processor unit having an image processing circuit or a light source unit. A CCD 12 provided with the same color filters as those described for FIG. 14 is set to the front end of the scope 10 and a light guide 15 for guiding the light of a light source lamp 14 up to the front end is set to the scope 10. Moreover, a freeze switch 16 for displaying a static image is set to the operating section of the scope 10.

A CCD driving circuit 18 for driving the CCD 12 is connected to the CCD 12, a timing generator 19 and a microcomputer 20 for performing various types of control are connected to the driving circuit 18, and the operation signal of the freeze switch 16 is input to the microcomputer 20. The CCD driving circuit 18 receives a timing signal in accordance with the control by the microcomputer 20 and controls the under-CCD-outputting pixel-mixing read mode for dynamic images and the every-pixel read mode for static images.

For example, the every-pixel read mode supplies two types of pulses for reading the accumulated data for all pixels accumulated in the CCD 12 through one-time exposure by dividing the accumulated data into odd-line data and even-line data and temporally shifting both the data values from each other from the CCD driving circuit 18 and performs the control for successively and separately reading the odd-line signals and the even-line signals from the CCD 12 in accordance with the two types of pulses. The under- CCD-outputting pixel-mixing read mode supplies one type of read pulse to each line.

In the case of a light source section for supplying light to the light guide 15, a diaphragm plate 22 for adjusting the outgoing luminous energy, a shading mask 23, and a shading shutter (plate) 24 for setting a shading period are set between the light source lamp 14 and the incoming end of the light guide 15. A motor 25 and a control circuit 26 are connected to the diaphragm plate 22 and a motor 27 and a shading-shutter control circuit 28 are connected to the shading shutter 24. Moreover, the lamp 14 is turned on/off by a lamp driving circuit 29.

Moreover, the diaphragm control circuit 26 drives the diaphragm plate 22 in accordance with a brightness signal obtained by a DVP (39) to be described later to adjust the outgoing luminous energy of the lamp 14. Furthermore, the shading-shutter control circuit 28 drives the shading shutter 24 at a predetermined timing after the freeze switch 16 is pressed to completely shade light for a predetermined shading period of 1/60 sec.

Figure 2:
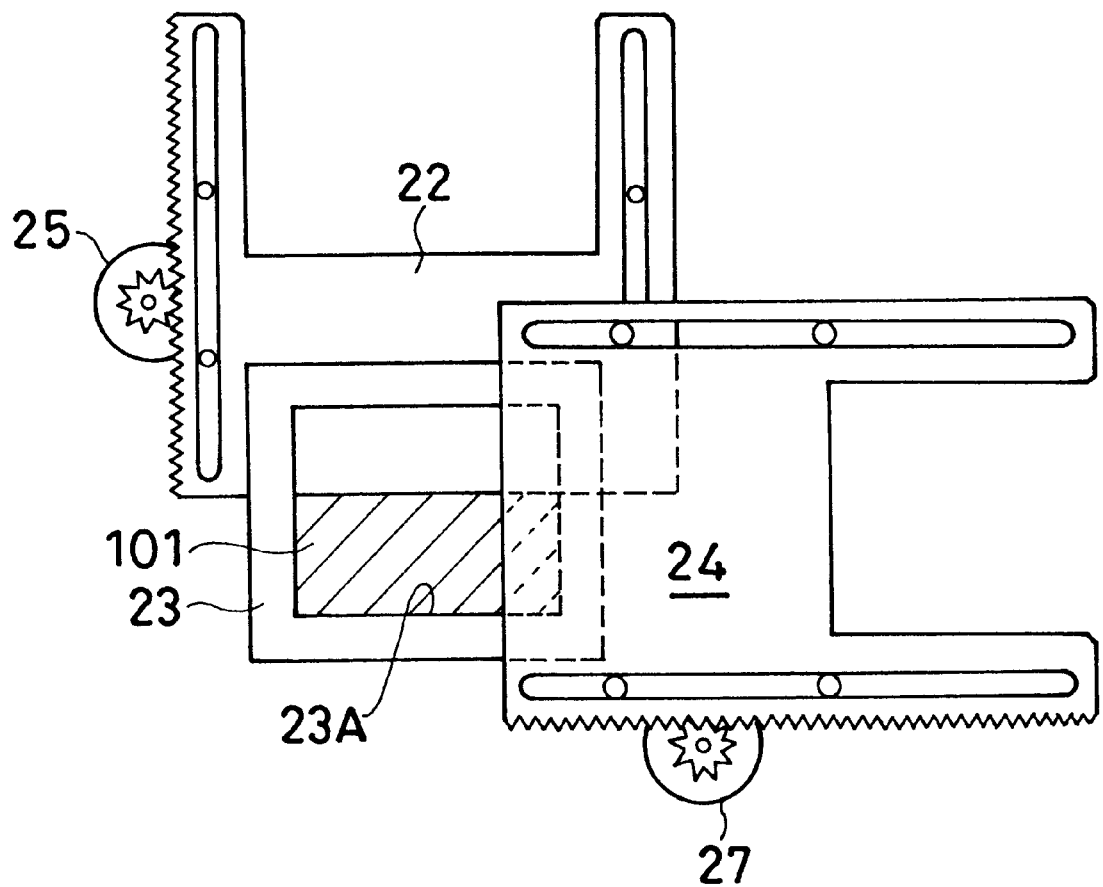
FIG. 2 is an illustration showing the arrangement of the diaphragm member, shading plate, and shading shutter of the first embodiment.

FIG. 2 shows the arrangement of the diaphragm plate 22, shading mask 23, and shading shutter 24. As shown in FIG. 2, a rectangular (or square is also permitted) opening 23A is formed on the shading mask 23, the diaphragm plate 22 is vertically movably set along the right and left sides of the rectangular opening 23A, and the diaphragm plate 22 is vertically driven by the motor 25. Moreover, the shading shutter 24 is horizontally movably set along the top and bottom sides of the opening 23A and horizontally driven by the motor 27.

Thus, the shading shutter 24 and the diaphragm plate 22 move in directions perpendicular to each other. Therefore, even if the diaphragm plate 22 for vertically moving the opening 23A is present at any diaphragm position, the shading shutter 24 for completely shading an actual luminous flux 101 moves from the left end to the right end of the opening 23A without fail. Therefore, the response time of the shading shutter 24 becomes always the same.

In FIG. 1, an amplifier 31 constituted with an automatic gain circuit (AGC) and the like is provided for the rear stage of the CCD 12 and the amplifier 31 makes it possible to amplify the luminous-energy deficiency caused by setting a shading period by the shading shutter 24. The amplifier 31 is provided with a first memory 33 for storing the odd-line image data in order to read every pixel through an A/D converter 32, a second memory 34 for storing even-line image data, a phase-adjusting third memory 35 for directly storing the data of the first memory 33 and delaying the read timing by 1/60 sec, and a static-image mixing circuit 36.

That is, all pixel signals obtained by the CCD 12 are divided into odd-line data and even-line data and temporarily stored in the memories 33 and 34. However, by delaying the odd-line data in the first memory 33 by 1/60 sec, the phase of the odd-line data becomes the same as that of the even-line data stored in the second memory 34. Thereby, both image data values are simultaneously read and thus, the mixing circuit 36 at the next stage is able to add and mix the odd-line pixel data in the third memory 35 and the even-line pixel data in the second memory 34 with each other (static-image pixel mixing). Therefore, in the case of a static image, a pixel-mixed signal equivalent to the case of the conventional color-difference successive-mixing read mode is formed by the mixing circuit 36.

FIGS. 4(A) to 4(E) show the contents of the static-image data to be processed by the circuits between the CCD 12 and the mixing circuit 36. As shown in FIG. 4(A), horizontal lines 0 to N are set in the CCD 12 correspondingly to the number of scanning lines and the pixel data values in the horizontal lines are transferred to a transfer line and read. Moreover, the data values of the odd lines (lines 1, 3, 5, . . . ) in the CCD 12 are stored in the first memory 33 (and the third memory 35) of FIG. 4(B) and the data values of the even lines (lines 2, 4, 6, . . . ) are stored in the second memory 34 of FIG. 4(C).

The data values in the memories 35 and 34 are pixel-mixed between the lines of FIGS. 4(B) and 4(C) by the mixing circuit 36 and addition data values of the lines 0+1, lines 2+3, lines 4+5, are output as odd-field data as shown in FIG. 4(D). Moreover, pixel mixing is performed between the lines of FIG. 4(B) while the read lines of FIG. 4(C) are respectively shifted downward by one line (data values are read from the illustrated position C1) and addition data values of the lines 1+2, lines 3+4, lines 5+6, . . . are output as even-field data as shown in FIG. 4(E).

In FIG. 1, an image change circuit 38 for changing a dynamic image and a static image is provided for the rear stage of the mixing circuit 36. In the case of the image change circuit 38, the output of the A/D converter 32 is supplied to the terminal "a" of the circuit 38 through a line L in order to form a dynamic image and the output of the mixing circuit 36 is supplied to the other terminal "b" of the circuit 38. When the freeze switch 16 is pressed, the terminal "a" is changed to the terminal "b." A DVP (Digital Video Processor) 39 is connected to the image change circuit 38. In the DVP 39, various types of processing including gamma control are performed and a color-difference signal or brightness signal is generated. A memory for storing odd- and even-field data values and a D/A converter are provided for the rear stage of the DVP 39 and a video signal is output to a monitor through the D/A converter.

Figure 3:
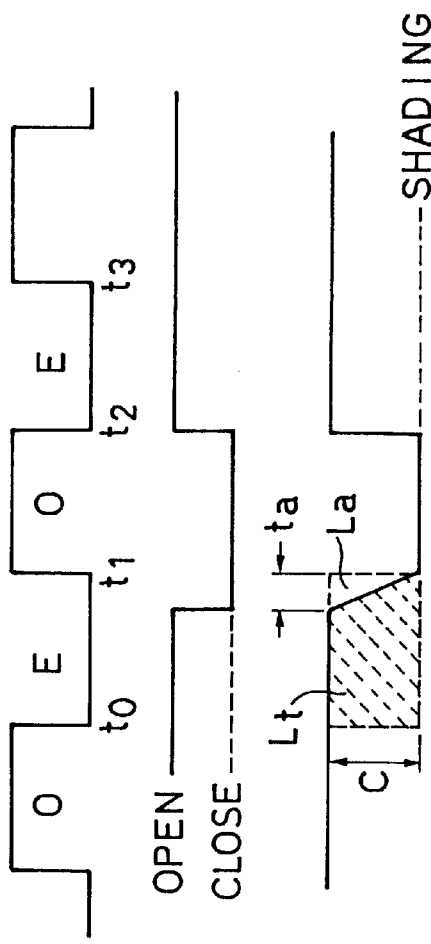
FIGS. 3(A) to 3(F) are waveform diagrams showing the signal read operation when forming a static image in an embodiment.

The embodiment is constituted as described above and its functions are described below by referring to FIGS. 3 and 4. As shown in FIG. 3(A), a timing signal for forming a one-field image for 1/60 sec is used as a field O(Odd)/E(Even) signal as ever. Under the normal state, the embodiment is set so as to execute dynamic-image processing, that is, the under-CCD-outputting pixel-mixing read mode. The shading shutter 24 of FIG. 1 is set to a position not shading a light-source luminous flux and the light emitted from the light source lamp 14 is irradiated into an object to be observed from the front end through the light guide 15.

According to the above light irradiation, electric charges corresponding to the image light emitted out of the object to be observed are accumulated in the CCD 12 at the front end. In the case of the accumulated electric charges, the pixels between upper and lower lines are read in accordance with driving pulses supplied from the CCD driving circuit 18 and the pixel-mixed signal described for FIG. 14 is output as ever. Moreover, the dynamic-image signal is supplied to the image change circuit 38 from the A/D converter 32 through the through-line L and supplied to the DVP 39 through the terminal "a" of the image change circuit 38. Operations after the DVP 39 are the same as ever and a dynamic image is displayed on a monitor in accordance with odd- and even-field signals.

In this case, the brightness signal obtained by the DVP 39 is supplied to the microcomputer 20, the diaphragm plate 22 is driven in accordance with the control by the microcomputer 20 and the diaphragm control circuit 26, and thereby the brightness of an image is kept constant.

When the freeze switch 16 of the scope 10 of FIG. 1 is pressed, the terminal of the image change circuit 38 is changed to the terminal "b" by the microcomputer 20 and the pixel-mixing read mode is changed to the every-pixel read mode for a static image. Then, as shown in FIG. 3(B), the shading shutter 24 shades the luminous flux 101 only for approx. 1/60 sec slightly before the rise time (t1) of the O/E signal and the light output from the light source section is shaded as shown in FIG. 3(C). Therefore, the image data from which every pixel is read becomes electric charges accumulated in the CCD 12 by an optical output Lt in a period of 1/60 sec just before a shading period.

That is, FIG. 3(D) shows a read pulse P1 for the odd lines shown in FIG. 4(B) and FIG. 3(E) shows a read pulse P2 for the even lines shown in FIG. 4(C). As illustrated, odd-line data and even-line data are successively read from the CCD 12 in accordance with the read pulse P1 from which the pulse at the time of t2 is removed and the read pulse P2 from which the pulse at the time of t1 is removed. Therefore, odd lines are read in the shading period (t1–t2) and even lines are read in the shading period (t2–t3).

Moreover, FIG. 3(F) shows operations of an electronic shutter, in which electric charges accumulated in the rise period of a pulse are discharged and electric charges out of the rise period of the pulse are read. Therefore, the above static-image data (accumulated electric charges) is obtained through the exposure g1 for the exposure time tb after electric charges are discharged and the electric charges of all pixels are read by the CCD driving circuit 18. Moreover, electric charges are not discharged in the shading period (t1–t2) after the exposure g1.

Figure 16:
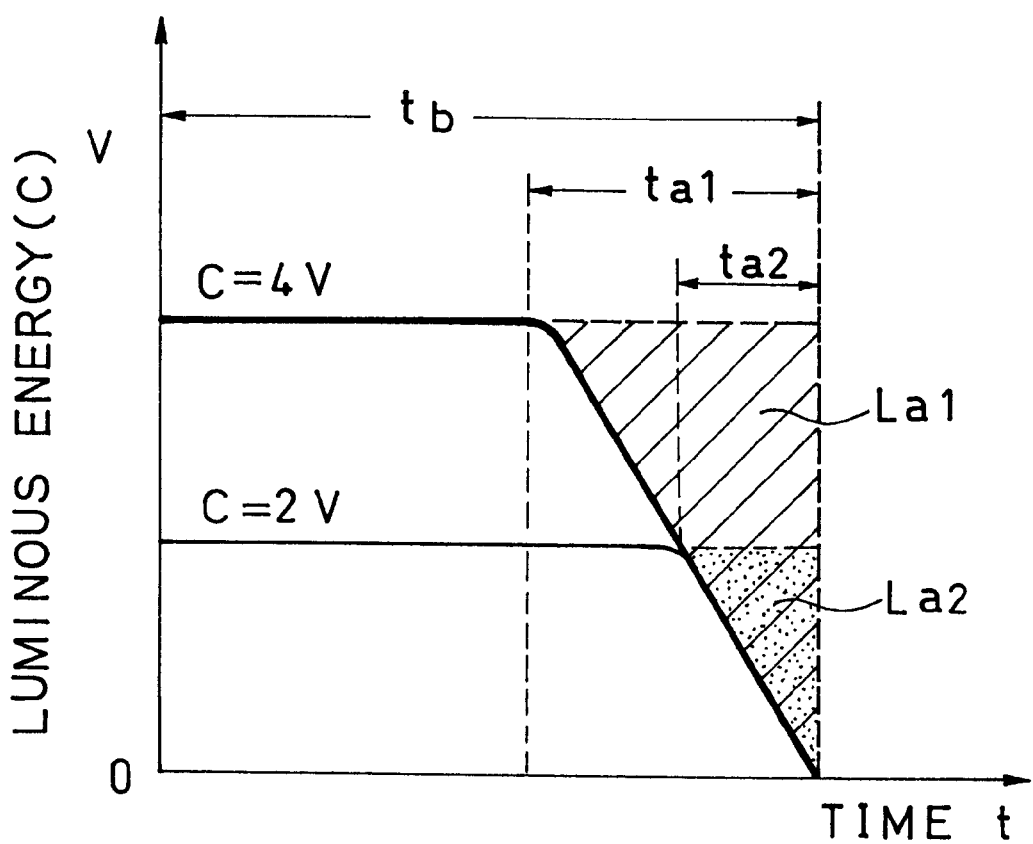
FIG. 16 is an illustration showing the relation between response time of the shading shutter and insufficient luminous energy in the unit of FIG. 15.

Because it is necessary to prevent unnecessary electric charges from being accumulated in the CCD 12 by setting a complete shading state in the above shading period, the control considering a response time is performed. That is, the shading-shutter control pulse of FIG. 3(B) is formed so as to be reversed early by a mechanical response delay time ta (response time) of the driving section (including a gear and the like) of the shading shutter 24. Thus, when the shading shutter 24 is driven, the light emitted from the light source section attenuates like a quadratic curve for the response time ta as shown in FIG. 3(C) or FIG. 16 and thereafter, a complete shading state is realized. Therefore, the optical output Lt for a static image loses a luminous energy equivalent to the loss of a luminous energy La.

Moreover, as described in FIG. 16, the response time ta has depended on a diaphragm opening degree so far. In the case of this embodiment, however, because the rectangular opening 23A is provided for the shading mask 23 and the shading shutter 24 is moved so as to perpendicularly intersect the moving direction of the diaphragm plate 22, the response time ta of the shading shutter 24 becomes the same independently of the position of the diaphragm plate 22 as shown in FIG. 2.

Figure 5:
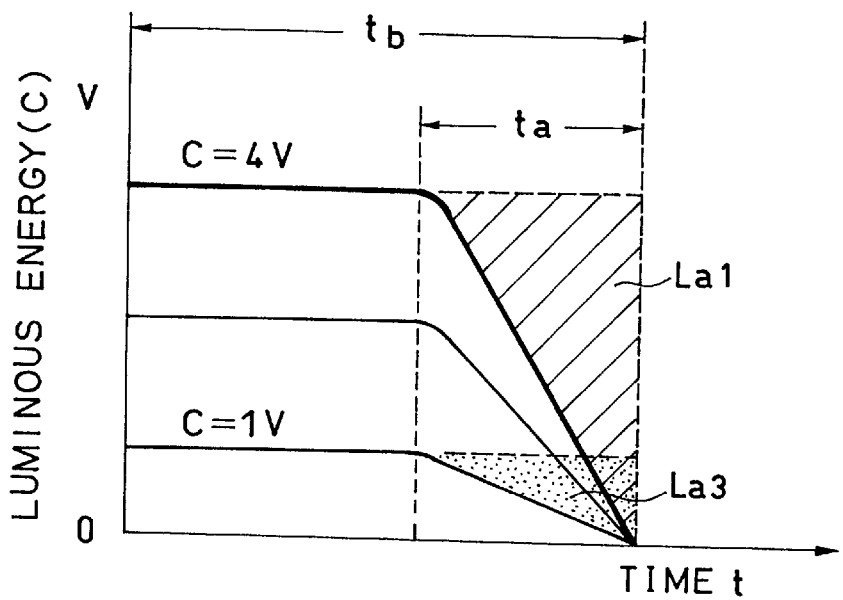
FIG. 5 is an illustration showing the relation between response time of a shading shutter and insufficient luminous energy in an embodiment.

FIG. 5 shows the relation between luminous energy C (light quantity) of the luminous flux 101 passing the opening 23A of this embodiment and response time. In this case, by comparing the insufficient luminous energy La1 when the diaphragm plate 22 fully opens with the insufficient luminous energy La3 when the diaphragm plate 22 is slightly driven, it is understood that the rate of insufficient luminous energy to the whole exposure value becomes constant depending on a certain response time even if the luminous energy C is changed by the diaphragm plate 22.

First, when the diaphragm plate 22 fully opens and it is assumed that the luminous energy C for unit time is equal to 4 V, the response time ta is equal to ta1=2 mS (sec), and the exposure time (tb) is equal to 1/60 sec, the dynamic-image electric charge quantity accumulated in the CCD 12 reaches 66.67 [mVS] and the static-image electric charge quantity when setting a shading period reaches approx. 62.67 [mVS] similarly to the case of FIG. 16. Therefore, the luminous energy of the static image results in 94% of the luminous energy of a dynamic image and the insufficient luminous energy La1 results in 6% of the whole luminous energy.

Then, when the diaphragm plate 22 is slightly driven and it is assumed that the luminous energy C is equal to 1 V, the response time ta is equal to 2 mS, and the exposure time tb is equal to 1/60 sec, the dynamic-image electric charge quantity accumulated in the CCD 1 is obtained from the following expression.

$$tb \times C = 1/60[mS] \times 1[V] \approx 16.67[mVS]$$

Moreover, the static-image electric charge quantity when setting a shading period is obtained from the following expression by assuming the attenuation line of the response time ta as a straight line.

$$tb \times C - (1/2)ta \times C = 1/60[mS] \times 1[V] - (1/2) \cdot 2[mS] \times 1[V] \approx 15.67[mVS]$$

Therefore, also in this case, the luminous energy of the static image results in 94% of the luminous energy of the dynamic image and the insufficient luminous energy La3 results in 6% of the whole luminous energy. Thus, even if the diaphragm opening degree differs, the rate of the insufficient luminous energy of the static image does not change.

As a result, the fluctuation of luminous energy reduction caused by setting a shading period is eliminated and it is possible to obtain a static-image signal having a preferable brightness (luminance) even if an object to be observed is present at a far point or a near point. Moreover, as described above, it is possible to compensate the luminous energy reduction of 6% with the amplifier 31 or the like.

Thus, in the case of the static-image signal obtained by the CCD 12 through the above luminous energy control, the odd-line data is written in the first memory 33 of FIG. 1, the even-line data is written in the second memory 34, the odd-line data in the first memory 33 is delayed by 1/60 sec by the third memory 35, and the phase of the odd-line data is matched with that of the even-line data in the second memory 34.

Then, the data values stored in the memories 35 and 34 are pixel-mixed by the mixing circuit 36, the addition data values of the lines 0+1, lines 2+3, . . . shown in FIG. 4(D) are output as odd-field data from the mixing circuit 36, and the addition data values of the lines 1+2, lines 3+4, . . . shown in FIG. 4(E) are output as even-field data. A static image is displayed on a monitor in accordance with these field data values and the static image has a high quality because it is formed with all pixel data values obtained through one-time exposure. Therefore, even if an endoscope or an object to be observed is moved for 1/60 sec, it is possible to observe a clear static image hardly influenced by the movement of the endoscope or object. Moreover, it is possible to obtain a dynamic image accurately reproducing the movement of an object.

Figure 6:
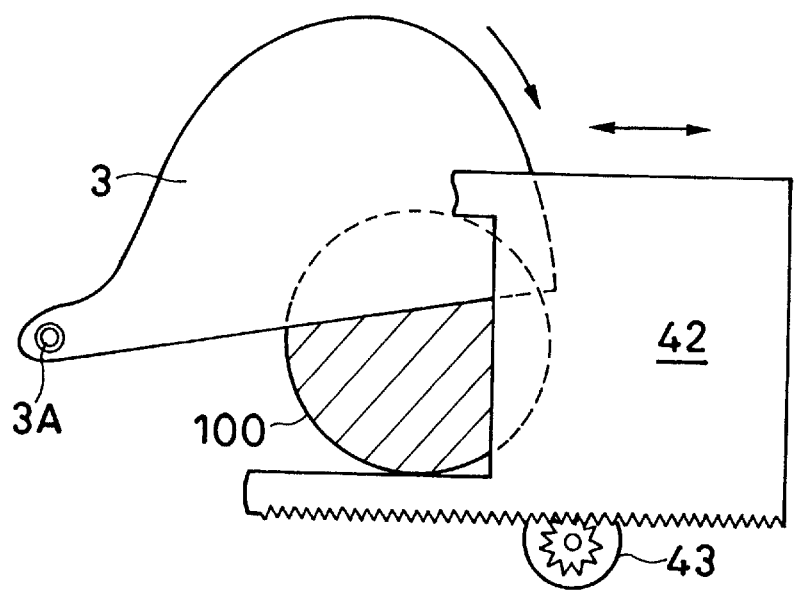
FIG. 6 is an illustration showing the structure of the second embodiment related to a diaphragming mechanism of the present invention.
Figure 15:
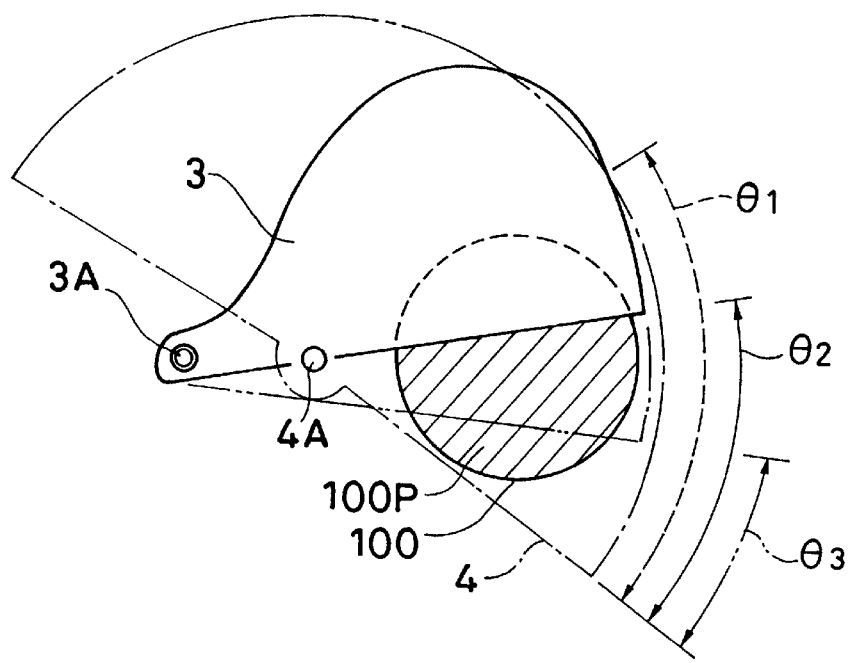
FIG. 15 is an illustration showing the arrangement of the diaphragm vane and shading shutter of a conventional light source unit.

Second Embodiment:

FIG. 6 shows the second embodiment related to a diaphragming mechanism. This embodiment is provided with a diaphragm vane 3 so as to shade a circular luminous flux (opening) 100 similarly to the case of the conventional diaphragm vane of FIG. 15, in which a shading shutter 42 for shading the luminous flux 100 is horizontally movably set to drive the shading shutter 42 with a motor 43. In this case, the diaphragm vane 3 rotates about a rotation axis 3A to vertically move and the shading shutter 42 horizontally moves so as to almost perpendicularly intersect the moving direction of the vane 3.

Also according to the above structure, it is possible to keep the response time of the shading shutter 42 almost constant except the time when the shutter is greately diaphragmed and obtain a static image having a stable brightness because the change of insufficient luminous energy due to the response time is controlled.

This embodiment accurately reproduces the movement of an object by using the under-outputting mixing read mode of the CCD 12 for a dynamic image. Even when following up a clear image having no movement for this dynamic image, it is possible to use the every-pixel read mode using a shading period for dynamic image formation.

As described above, according to the first and second embodiments, the response time of a shading shutter becomes constant even if the diaphragm opening degrees are different from each other and thus, it is possible to eliminate the fluctuation of luminous energy reduction. Therefore, even in the case of the every-pixel read mode using a shading period, it is possible to obtain an image having a stable brightness independently of an image pickup distance and the like.

Third Embodiment

Figure 7:
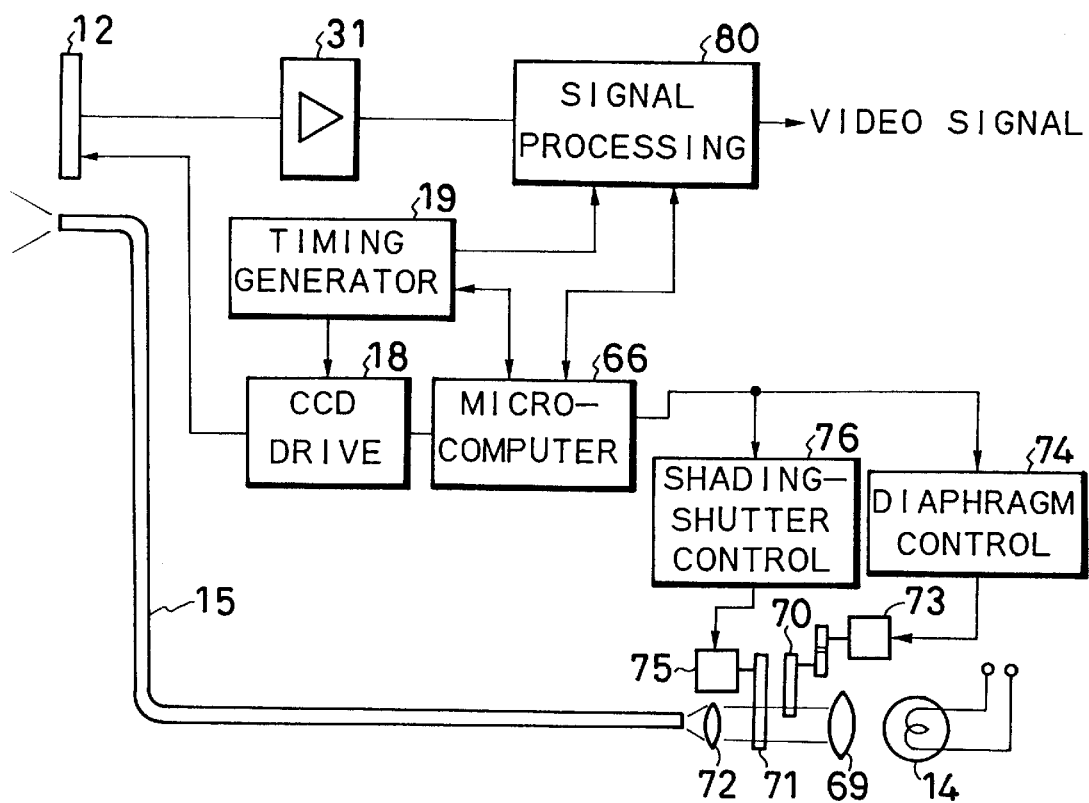
FIG. 7 is a block diagram showing a schematic structure of an electronic endoscope system to which the light source unit of the third embodiment is applied.
Figure 8:
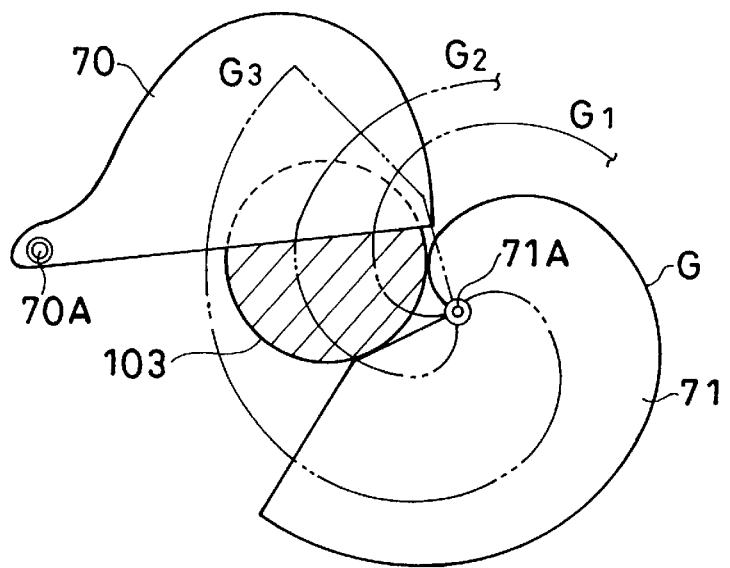
FIG. 8 is an illustration showing the arrangement of the diaphragm vane and shading shutter of the electronic-endoscope light source unit of the third embodiment.
Figure 9:
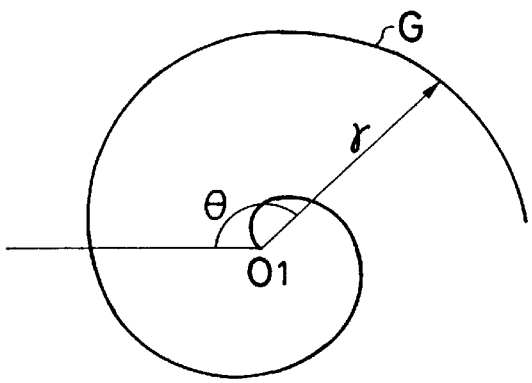
FIG. 9 is an illustration showing the Archimedean spiral on the outer periphery of the shading shutter of FIG. 8.

FIGS. 7 to 9 show the structure of the electronic endoscope system of the third embodiment. Also in the case of the third embodiment, as shown in FIG. 7, a CCD 12 image-picks up the inside of an object through the irradiation with the light supplied through a light guide 15 and connects with a CCD driving circuit 18, a timing generator 19, and a microcomputer 66 for performing various controls. The CCD driving circuit 18 drives and controls the under-CCD-outputting pixel-mixing read mode for dynamic images and the every-pixel read mode for static images similarly to the case of the first embodiment.

Moreover, a light source section for supplying light to the light guide 15 is provided with a light source lamp 14, a condenser lens 69, a diaphragm vane 70 for adjusting outgoing luminous energy, a shading shutter (plate) 71 for setting a complete shading period, and a condenser lens 72 are arranged between the lamp 14 and the incoming end of the light guide 15, a motor 73 and a diaphragm control circuit 74 are connected to the diaphragm vane 70, and a motor 75 and a shading-shutter control circuit 76 are connected to the shading shutter 71.

The diaphragm control circuit 74 drives the diaphragm vane 70 in accordance with a brightness signal obtained by a signal processing circuit (80) to be described later and adjusts the outgoing luminous energy of the lamp 14. Moreover, the shading-shutter control circuit 76 drives the shading shutter 71 at a predetermined timing after a freeze switch set to a scope operating section or the like is pressed to completely shade light for a predetermined shading period of 1/60 sec.

FIG. 8 shows arrangement of the diaphragm vane 70 and the shading shutter 71. As shown in FIG. 8, the diaphragm vane 70 is set so as to rotate about an axis 70A and shade a light-source luminous flux (or diaphragm opening) 103 in accordance with a diaphragm value as similarly to the conventional case. Moreover, the outer periphery G of the shading shutter 71 is formed like the Archimedean spiral and set so as to rotate about an axis 71A.

That is, FIG. 9 shows the Archimedean spiral. The spiral can be shown as a spiral having a length r of a θ (a: positive coefficient) from a center O1 in accordance with polar coordinates (r, θ). By rotating the shading shutter 71 having the Archimedean-spiral outer periphery G about the axis 71A counterclockwise, the outer-periphery position moves from G1 to G2 and G3 as illustrated in the direction almost perpendicular to the shading direction of the diaphragm vane 70 to completely shade the light-source luminous flux 103.

Thereby, even if the diaphragm vane 70 for slowly shading the luminous flux 103 is present at any position after moving from upper side to lower side, the outer periphery G of the shading shutter 71 rotates while moving for a constant distance from the right end of the luminous flux 103 up to the left end of it without fail and thus, completely shades the then luminous flux 103. Therefore, the response time of the shading shutter 71 is always kept constant (except the time when the shutter 71 is greatly diaphragmed).

In the case of the above structure, it is also possible to provide a shading plate having a quadrangular opening such as a rectangular opening for a diaphragming mechanism section, set a diaphragm plate so as to linearly move in the vertical direction of the rectangular opening, and set the shading shutter (71) so as to move in the horizontal direction of the rectangular opening. Thereby, because the rectangular opening is slowly diaphragmed in the vertical direction from the upper side, even if the diaphragm is greatly diaphragmed, the response time for the shading shutter to shade the then luminous flux 103 always becomes constant.

In FIG. 7, an amplifier 31 constituted with an automatic gain circuit (AGC) is set to the rear stage of the CCD 12, which is also able to amplify the luminous energy deficiency produced due to setting of a shading period by the shading shutter 71. A signal processing circuit 80 including a memory and the like is connected to the amplifier 31, which performs the same processing as the case of the first embodiment.

Figure 10:
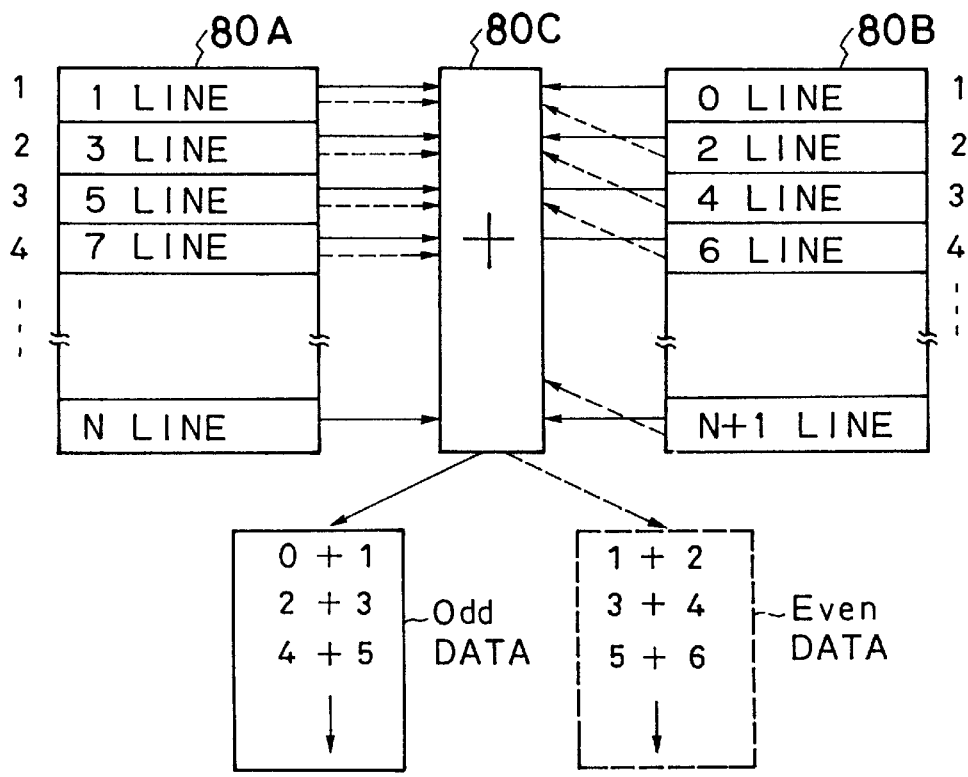
FIG. 10 is an illustration showing the video data to be processed by the signal processing circuit of the third embodiment.

FIG. 10 shows static-image data processing contents performed by the signal processing circuit 80 and the contents are the same as the operations shown in FIG. 4. Data values of odd lines (lines 1, 3, 5, . . . ) of the CCD 12 are stored in one memory 80A as shown at the left of FIG. 10 and data values of even lines (lines 2, 4, 6, . . . ) of the CCD 12 are stored in the other memory 80B as shown at the right of FIG. 10.

Both the data values in the memories 80A and 80B are pixel-mixed by a mixing circuit 80C from the upper side in order as shown by continuous- or dotted-line arrows, the addition data values of lines 0+1, lines 2+3, . . . shown by continuous lines are output as odd-field data and the addition data values of lines 1+2, lines 3+4, . . . shown by chain lines are output as even-field data.

The third embodiment is constituted as described above to perform the same operations as those of FIG. 3 even in the case of this example. That is, an image is formed in accordance with the field O(Odd)/E(Even) for 1/60 sec. In the case of normal dynamic-image processing, the under-CCD-outputting pixel-mixing read mode is executed. The shading shutter 71 of FIGS. 8 and 9 is set to a position which does not shade the light-source luminous flux 103 and the light emitted from the light source lamp 14 is applied into an object to be observed from the front end through the light guide 15.

Moreover, a pixel-mixed signal obtained by the CCD 12 is supplied to the signal processing circuit 80. Thus, odd- and even-field signals are generated and thereby, a dynamic image is displayed on a monitor. In this case, a brightness signal obtained by the signal processing circuit 80 is supplied to the microcomputer 66, the diaphragm vane 70 is driven in accordance with the control by the microcomputer 66 and the diaphragm control circuit 74, and thereby the brightness of an image is kept constant.

When the freeze switch is pressed, the present mode is changed to the every-pixel read mode for static images by the microcomputer 66. Then, the shading shutter 71 completely shades the luminous flux 103 only for approx. 1/60 sec starting with the time slightly before the rise time (t1) of the O/E signal shown in, for example, FIG. 3(B) and light is shaded during the period as shown in FIG. 3(C). Moreover, the odd-line data values shown at the left of FIG. 10 and the even-line data values shown at the right of FIG. 10 are successively read out of the CCD 12 in accordance with the read pulses P1 and P2 shown in FIGS. 3(D) and 3(E). The static-image data is obtained through the exposure g1 for an exposure time tb after electric charges are discharged as shown by the electronic-shutter operation of FIG. 3(F).

Furthermore, for the shading-shutter control pulse of FIG. 3(B), a pulse is formed which is reversed early by a mechanical response delay time (response time) ta of the driving section (including gears and the like) of the shading shutter 71. Therefore, an optical output Lt for a static image loses luminous energy by the loss of a luminous energy La. That is, as described for FIG. 16, the response time ta has been changed so far depending on a diaphragm opening degree. In the case of the third embodiment, however, because the outer periphery G of the shading shutter 71 is formed like the Archimedean spiral and the outer periphery G moves in a direction almost perpendicular to the shading direction of the diaphragm vane 70, the then actual luminous flux 103 is always shaded in accordance with the movement of the shading shutter 71 from the left end up to the right end independently of the moving position of the diaphragm vane 70 and the response time ta of the shutter 71 is always kept constant.

Moreover, the relation between luminous energy (C) of the luminous flux 103 and response time becomes the same as the relation described for FIG. 5. Therefore, even if the luminous energy C is changed due to the diaphragm vane 70, the rate of insufficient luminous energy to the whole luminous energy is kept constant in accordance with a constant response time. That is, when the diaphragm vane 70 fully opens, the luminous energy of a static image is equal to 94% of the luminous energy of a dynamic image and an insufficient luminous energy La1 results in 6% of the whole luminous energy. Also when the diaphragm vane 70 is slightly driven, the luminous energy of a static image is equal to 94% of the luminous energy of a dynamic image and the insufficient luminous energy La3 results in 6% of the whole luminous energy. The luminous energy reduction of 6% can be compensated by the amplifier 29 or the like.

Fourth Embodiment

Figure 11:
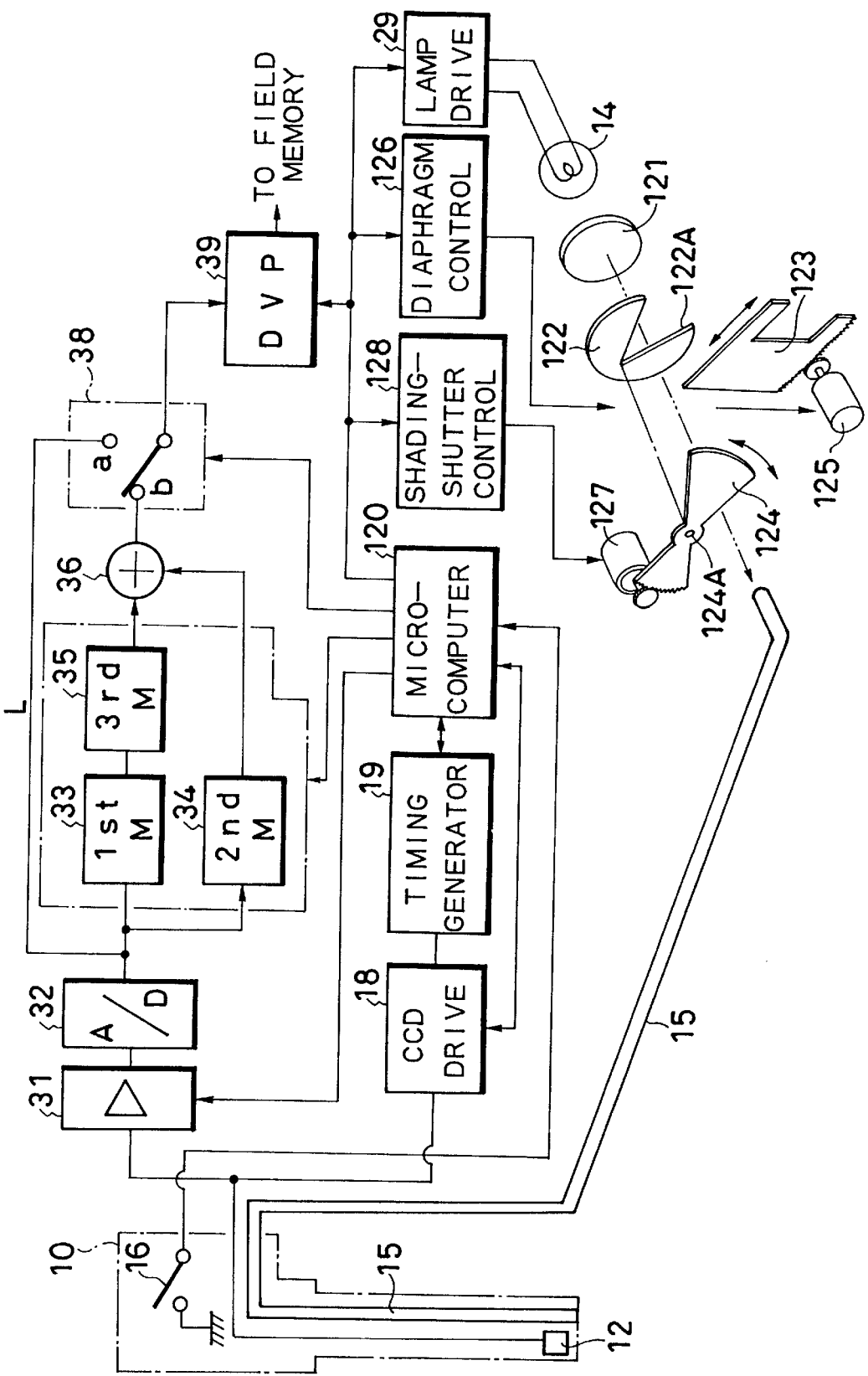
FIG. 11 is an illustration showing the entire structure of an electronic endoscope system to which the light source unit of the fourth embodiment is applied.

FIG. 11 shows the structure of the electronic endoscope system of the fourth embodiment. The structure of the electronic endoscope system is the same as the case of the first embodiment except the light source section. Moreover, the CCD driving circuit 18 of FIG. 11 drives and controls the under-CCD-outputting pixel-mixing read mode for dynamic images and the every-pixel read mode for static images in accordance with the control by a microcomputer 20 and the static-image data to be processed by circuits between a CCD 12 and a mixing circuit 36 becomes the same as the content described for FIG. 10.

In the case of a light source section for supplying light to the light guide 15, a condenser lens 121 and a shading mask 122 for controlling a luminous flux are arranged between the light source lamp 14 and the light guide 15 and a V-shaped opening 122A is formed on the shading mask 122. Moreover, a diaphragm plate 123 to be horizontally moved to adjust outgoing luminous energy and a shading shutter (plate) 124 to be rotated to set a complete shading period are arranged, a motor 125 and a diaphragm control circuit 126 are connected to the diaphragm plate 123, and a motor 127 and a shading-shutter control circuit 128 are connected to the shading shutter 124. Moreover, the lamp 14 is turned on/off by a lamp driving circuit 29.

Furthermore, the diaphragm control circuit 126 drives the diaphragm plate 123 in accordance with a brightness signal obtained by a DVP 39 to adjust the outgoing luminous energy of the lamp 14. Furthermore, the shading-shutter control circuit 128 drives the shading shutter 124 at a predetermined timing after the freeze switch 16 is pressed to completely shade light for a predetermined shading period of 1/60 sec.

Figure 12:
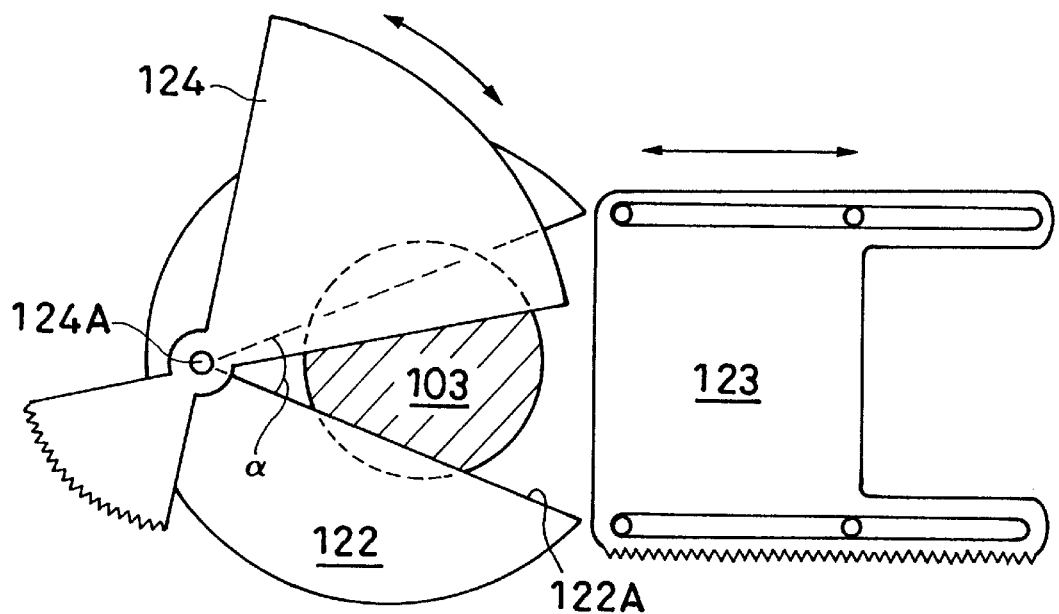
FIG. 12 is an illustration showing the arrangement of the shading plate, diaphragm member, and shading shutter of the fourth embodiment.

FIG. 12 shows the arrangement of the shading mask 122, diaphragm plate 123, and shading shutter 124. As illustrated, a V-shaped (opening angle of α) opening 122A having a size for shading a part of a light-source luminous flux 103 is formed on the shading mask 122, the shading shutter 124 is formed like a sector so as to be able to shade the V-shaped opening, the rotation axis 124A of the shading shutter 124 is set to the position of the V-shape intersection of the V-shaped opening 122A, and the shading shutter 124 rotates about the rotation axis 124A. The diaphragm plate 123 is set so as to be horizontally movable from the opening expanded side (upper side of V shape) of the V-shaped opening 122A toward the intersection, that is, along a line for dividing the opening angle α into two angles and moved almost perpendicularly to the moving direction of the shading shutter 24.

Thereby, even if the diaphragm plate 123 to be horizontally moved on the V-shaped opening 122A is present at any diaphragm position, the shading shutter 124 for completely shading the actual luminous flux 103 always rotates by the V-shape opening angle α of the opening 122A. Therefore, the response time of the shading shutter 124 is always kept constant.

The fourth embodiment is constituted as described above and its functions are the same as those of the above first to third embodiments. That is, the under-CCD-outputting pixel-mixing read mode is executed in the normal dynamic-image processing, the shading shutter 24 of FIG. 1 is set to a position not shading a light-source luminous flux, the light emitted from the light source lamp 14 is applied into an object to be observed from the front end through the light guide 15. Moreover, a brightness signal obtained by the DVP 39 is supplied to a microcomputer 120, the diaphragm plate 123 is driven in accordance with the control by the microcomputer 120 and the diaphragm control circuit 126, and thereby the brightness of an image is kept constant.

When the freeze switch 16 of the scope 10 of FIG. 1 is pressed, the present mode is changed to the every-pixel read mode for static images and the shading shutter 24 shades the luminous flux 103. During the above period, the light emitted from the light source section is shaded as shown in FIG. 3(C) and a shading period for 1/60 sec is set.

Moreover, it is necessary to prevent unnecessary electric charges from being accumulated in the CCD 12 by setting the above shading period to a complete shading state. Therefore, for the shading-shutter control pulse of FIG. 3(B), a pulse is generated which is reversed early by a mechanical response delay time (response time) ta of the driving section (including gears or the like) of the shading shutter 124. Therefore, an optical output Lt for a static image loses the luminous energy equivalent to the loss of luminous energy La and the response time ta is conventionally changed depending on a diaphragm opening degree. However, in the case of the fourth embodiment, because the V-shaped opening 122A is provided for the shading mask 122 and the shading shutter 124 is made to rotate about the V-shape intersection of the opening 122A, the actual luminous flux 103 is always shaded due to the rotation of the V-shape angle α of the shading shutter 124 independently of the moving position of the diaphragm plate 123 and thus, the response time ta of the shading shutter 124 is kept constant.

Furthermore, FIG. 5 shows the relation between luminous energy (C) of the luminous flux 103 passing the opening 122A of the fourth embodiment and response time. For example, as the result of comparing the insufficient luminous energy La1 when the diaphragm plate 123 fully opens with the insufficient luminous energy La3 when the diaphragm plate 123 is slightly driven, it is found that the rate of the insufficient luminous energy to the whole luminous energy also becomes constant in accordance with a certain response time even if the luminous energy C is changed due to the diaphragm plate 123. That is, when the diaphragm plate 123 fully opens, the luminous energy of a static image is equal to 94% of the luminous energy of a dynamic image and the insufficient luminous energy La1 results in 6% of the whole luminous energy. Also when the diaphragm plate 123 is slightly driven, the luminous energy of a static image is equal to 94% of the luminous energy of a dynamic image and the insufficient luminous energy La3 results in 6% of the whole luminous energy and even if diaphragm opening degrees are different from each other, the rate of the insufficient luminous energy of a static image becomes constant.

As a result, the fluctuation of luminous energy reduction caused by setting a shading period is eliminated and it is possible to obtain a static-image signal having a preferable brightness (luminance) even if an object to be observed is present at either of a far point and a near point. Moreover, as described above, the luminous energy reduction of 6% can be compensated by the amplifier 31 or the like.

The fourth embodiment uses the first shading means for a fully-closed shading mechanism having the shading shutter 124 and the second shading means for a diaphragming mechanism having the diaphragm plate 123. However, it is also possible to use the first shading means for the diaphragming mechanism and the second shading means for the fully-closed shading mechanism.

As described above, the fourth embodiment makes it possible to eliminate the fluctuation of luminous energy reduction by rotating a shading shutter about the V-shape intersection of the opening of a shading mask and linearly moving a diaphragm plate from the V-shaped opening expanded side toward an intersection.

Fifth Embodiment

Figure 13:
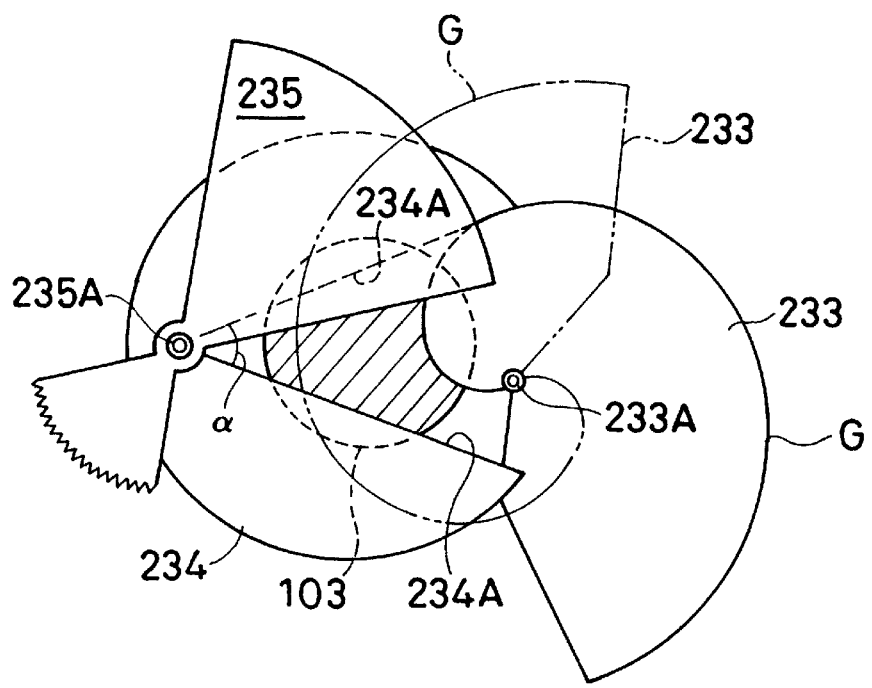
FIG. 13 is an illustration showing the arrangement of the diaphragm vane of the light source unit and the shading shutter of the fifth embodiment.

FIG. 13 shows the structure of the fifth embodiment. The fifth embodiment is constituted by combining the shading mask having the almost-V-shaped opening and the shading shutter of the fourth embodiment with the Archimedean-spiral diaphragm vane of the third embodiment. Structures other than these mechanisms are the same as those of the above embodiments. That is, description is started below with a component closest to a light source lamp (14). A diaphragm vane 233 whose outer periphery G is formed like the Archimedean spiral is connected to motors (75, 125) so as to rotate about the axis 233A of the vane 233 and a shading mask 234 for controlling a light-source luminous flux 103 by a V-shaped opening (V-shape opening angle α) 234A is set to the front side of the diaphragm vane 233.

Moreover, a sectorial shading shutter (plate) 235 for setting a shading period is set to the front side of the shading mask 234. The rotation axis 235A of the shading shutter 235 is set to the V-shape intersection of the V-shaped opening 234A and connected to a motor so as to rotate about the rotation axis 235A. Therefore, the shading shutter 235 and the diaphragm vane 233 are moved almost perpendicularly to each other.

According to the fifth embodiment, the actually used range of the light-source luminous flux 103 is controlled by the V-shaped opening 234A of the shading mask 234 and the diaphragm vane 233 shades a luminous flux emitted from the V-shaped opening 234A. That is, the diaphragm vane 233 diaphragms a luminous flux when the outer periphery G of the vane 233 horizontally moves from the opening expanded side (right of FIG. 13) of the V-shaped opening 234A toward the V-shape intersection (along a line for dividing the opening angle α into two angles) and sets a predetermined diaphragm value.

Moreover, the shading shutter 235 rotates about the V-shape intersection of the opening 234A. Thus, the shading shutter 235 for completely shading the then luminous flux always rotates by the V-shaped opening angle ( of the opening 234A even if the diaphragm vane 233 to be horizontally moved on the V-shaped opening 234A is present at any diaphragm position. Therefore, the response time of the shading shutter 235 is also kept constant and, even if an object to be observed is present at either of a far point and a near point, it is possible to obtain an image signal free from the fluctuation of luminous energy reduction and having a stable brightness.

What is claimed is:

1. An electronic-endoscope light source unit for setting a shading period, comprising:

first shading means for shading a light-source luminous flux in a predetermined shading direction;

second shading means for shading the light-source luminous flux in a shading direction almost perpendicular to the shading direction of the first shading means, wherein one of the first shading means and the second shading means is used as a diaphragming mechanism and the other shading means is used as a fully-closed shading mechanism for setting a fully-closed shading period for reading the signal of every pixel accumulated in an image pickup device; and wherein a shading mask having a quadrangular opening is set, and the diaphragm member of the diaphragming mechanism is made to move along the top and bottom sides or the right and left sides of the quadrangular opening, and the shading shutter of the fully-closed shading mechanism is moved along the other two sides.

2. An electronic-endoscope light source unit for setting a shading period, comprising:

first shading means for shading a light-source luminous flux in a predetermined shading direction;

second shading means for shading the light-source luminous flux in a shading direction almost perpendicular to the shading direction of the first shading means, wherein one of the first shading means and the second shading means is used as a diaphragming mechanism and the other shading means is used as a fully-closed shading mechanism for setting a fully-closed shading period for reading the signal of every pixel accumulated in an image pickup device; and wherein the second shading means has a shading member whose outer periphery is formed like the Archimedean spiral and the outer periphery of the shading member is made to move in a direction almost perpendicular to the shading direction of the first shading means so as to shade the light-source luminous flux.

3. An electronic-endoscope light-source unit for setting a shading period according to claim 2, wherein the first shading means has an edge which moves in a shading direction and which is approximately formed like a straight line.

* * * * *